US008388981B2

(12) United States Patent
Hoey et al.

(10) Patent No.: US 8,388,981 B2
(45) Date of Patent: Mar. 5, 2013

(54) ***BABESIA MICROTI* GENOMIC CLONES CONTAINING NOVEL ANTIGENS USEFUL IN THE DIAGNOSIS OF BABESIOSIS**

(75) Inventors: John G. Hoey, Framingham, MA (US); Hannah Venit, Cheltenham, PA (US); Martin E. Adelson, East Windsor, NJ (US); Eli Mordechai, Robbinsville, NJ (US); Fernando Valois-Cruz, Bordentown, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 0 days.

(21) Appl. No.: 13/440,106

(22) Filed: Apr. 5, 2012

(65) Prior Publication Data

US 2012/0202227 A1 Aug. 9, 2012

Related U.S. Application Data

(62) Division of application No. 12/386,097, filed on Apr. 14, 2009, now Pat. No. 8,178,310.

(51) Int. Cl.
*A61K 39/018* (2006.01)
*C07K 14/44* (2006.01)

(52) U.S. Cl. .................. 424/270.1; 424/191.1; 435/810; 530/300; 530/350

(58) Field of Classification Search ........................ None
See application file for complete search history.

(56) References Cited

U.S. PATENT DOCUMENTS 6,183,976 B1 * 2/2001 Reed et al. .................. 435/7.22
6,214,971 B1 * 4/2001 Reed et al. .................. 530/350

* cited by examiner

*Primary Examiner* — Padma Baskar
(74) *Attorney, Agent, or Firm* — Siu K. Lo, J.D.

(57) ABSTRACT

Disclosed are the cloning and expression of novel antigens in *Babesia microti*. The recombinant polypeptides are highly immunogenic. The polypeptides of the present invention provide the basis of a diagnostic assay that is sensitive, rapid and accurate using patient's sera. Also disclosed is an IgG and IgM ELISA using two novel recombinant antigens in the diagnosis of *Babesia* infection.

8 Claims, 14 Drawing Sheets

Figure 2

Babesia microti 5-1-1 Antigen

5-1-1 nucleotide sequence

Figure 3

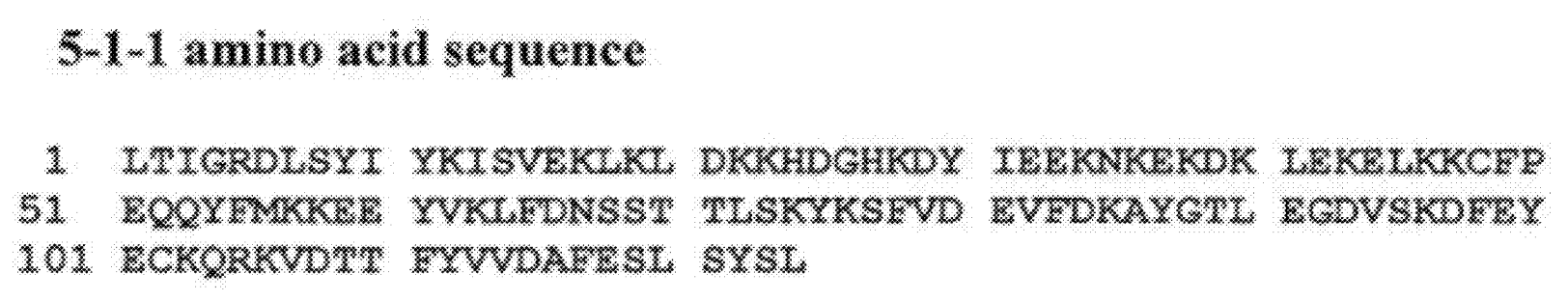

S-1-1 amino acid sequence

1   LTIGRDLSYI YKISVEKLKL DKKHDGHKDY IEKNKERDK LEKELKKCEP
51  EQQYMKEE YVKLFDNSST TLSKYKSFVD EVFDKAYGTL EGDVSKDFEY
101 ECKQRKVDTI FYVVDAFESL SYSL

Figure 4

BLAST Alignment of Antigen 5-1-1

Figure 6

*Babesia microti* 01-1-76 Antigen

Figure 7

O-1-1 76 amino acid sequence

1 MANEVKGAIEEVNKIIDVLVSNIRDSGYVIDNYIISSFKSVLSIINKIAQ
51 NINVSNVIPGLKALTLSVFLITIA

Figure 8

BLAST Alignment of Antigen 0-1-1 76

```
>gb|AAP88236.1|AF206245_1  seroreactive antigen BMN1-3 [Babesia microti]
Length=360

Score = 72.0 bits (175),  Expect = 1e-11, Method: Compositional matrix adjust.
Identities = 40/74 (55%), Positives = 52/74 (70%), Gaps = 5/74 (6%)

Query  1    MAHEVRGATEEVMKIDVLVSHIAPGGYIPNY--ISHKDVLSIIMEIAQNTNVSRVII    56
            M E+  A E +  +D++++ +I     Y  +S++   S+I +I +    +  VII
Sbjct  290  MLNELMSAAEGFNKYVDIMISHIGSD-----YDEVDIASPHPFLSMITSITKKYGNVII  344

Query  60   PGHKAITLKPYLIP    73
            PGHKAITL+PYLIP
Sbjct  346  PGHKAITLRPYLIP    359
```

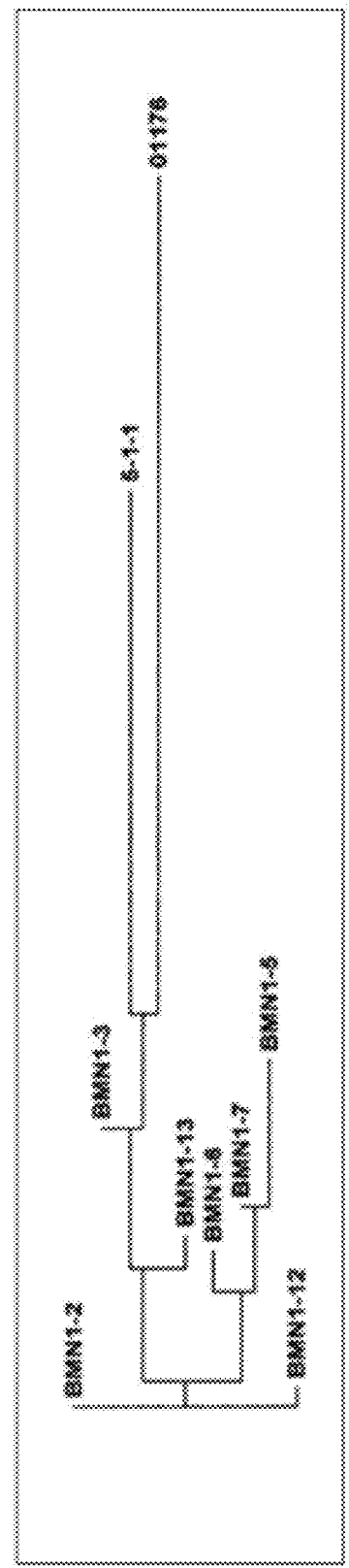
Figure 9. Phylogenetic relationship of 5-1-1 and 01-1 76 protein sequences with BMN family

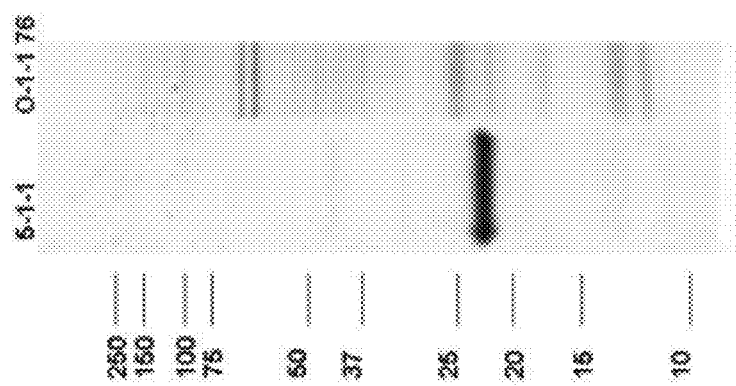
Figure 10 Coomassie-stained SDS PAGE gel of 5-1-1 and O-1-1 76

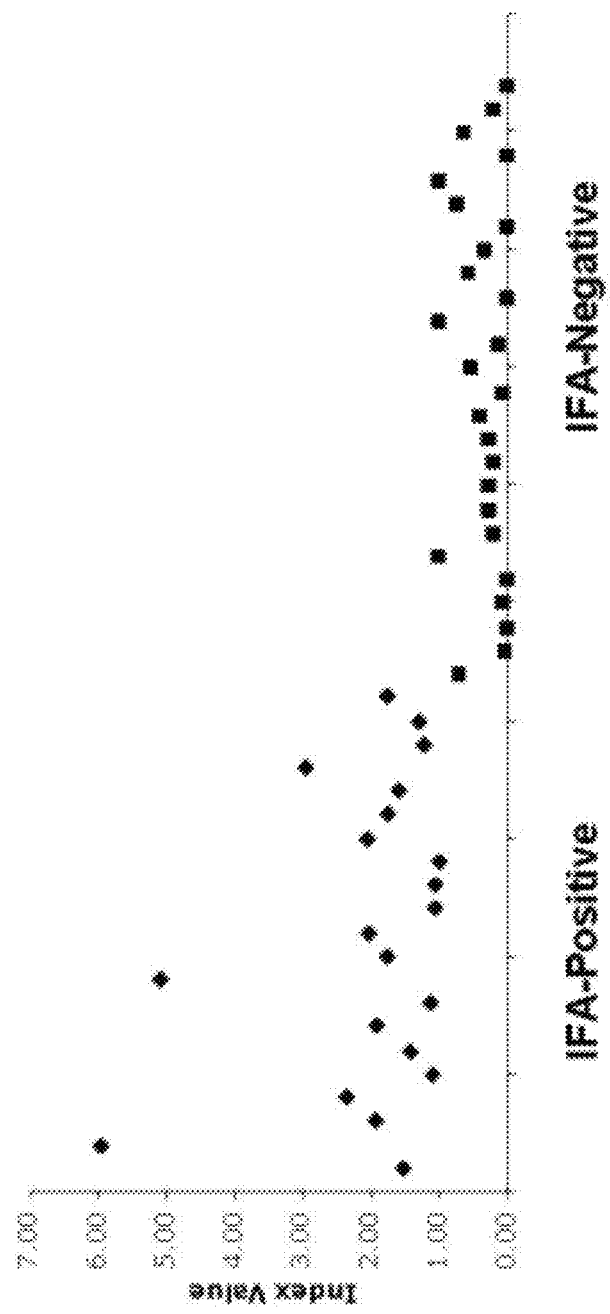

SEQUENCE LISTING

<160> NUMBER OF SEQ ID NOS: 8

<210> SEQ ID NO 1
<211> LENGTH: 372
<212> TYPE: DNA
<213> ORGANISM: Babesia microti

<400> SEQUENCE: 1

```
ctgactatcg ggagagattt atcttatata tacaaaatta gtgttgagaa actgaaacta      60
gataaaaagc atgatggtca taaagactac attgaagaaa aaaacaagga gaaggataaa     120
ttggaaaaag aattgaaaaa atgttttcct gaacaacaat actttatgaa gaagaagaa      180 tatgttaaat tatttgataa ttcgtctact acccttttcca aatataagtc atttgttgat    240
gaagtgttcg acaaggccta tggtacattg gaaggtgatg tttctaagga ttttgaatac    300
gaatgtaagc aaaggaaggt tgacacaact ttctatgtag tggacgcttt tgaatcactc    360
tcttacagct ta                                                         372
```

<210> SEQ ID NO 2
<211> LENGTH: 124
<212> TYPE: PRT
<213> ORGANISM: Babesia microti

<400> SEQUENCE: 2

```
Leu Thr Ile Gly Arg Asp Leu Ser Tyr Ile Tyr Lys Ile Ser Val Glu
1               5                  10                  15

Lys Leu Asp Lys Lys His Asp Gly His Lys Asp Tyr Lys Leu Ile Glu
            20                  25                  30

Glu Lys Asn Lys Glu Lys Asp Lys Leu Glu Lys Glu Leu Lys Lys Cys
        35                  40                  45

Phe Pro Glu Gln Gln Tyr Phe Met Lys Lys Glu Glu Tyr Val Lys Leu
    50                  55                  60

Phe Asp Asn Ser Ser Thr Thr Leu Ser Lys Tyr Lys Ser Phe Val Asp
65                  70                  75                  80

Glu Val Phe Asp Lys Ala Tyr Gly Thr Leu Glu Gly Asp Val Ser Lys
                85                  90                  95

Asp Phe Glu Tyr Glu Cys Lys Gln Arg Lys Val Asp Thr Thr Phe Tyr
            100                 105                 110

Val Val Asp Ala Phe Glu Ser Leu Ser Tyr Ser Leu
        115                 120
```

<210> SEQ ID NO 3
<211> LENGTH: 448
<212> TYPE: DNA
<213> ORGANISM: Babesia microti

<400> SEQUENCE: 3

```
atggccaatg aagtgaaagg tgcaattgaa gaagttaata aaattattga cgtcttggtt      60
tccaacatta gagatagtgg ttatgttatt gacaattata ttatttcaag cttcaaatct    120
gttctttcca taatcaacaa aatagcccaa aataccaacg tatctaatgt aataattcca    180
ggacttaagg cactaactct ttctgttttt ttaatattaa ctatagcttg aatgcaataa    240
```

-continued

```
cagatgtata cattattata tagtaccaaa tttacacaat attaaacatg agaagctcac    300
tcttaaataa agaaattgat atatatatgg aaatataatc aaagtaatag ggggatatat    360
ttgaatattg aaatatgtaa atctaaccga aataaatgaa gtaaaggat gtttgtatat     420 tgtatatcga atgaatacag aatataca                                      448
```

```
<210> SEQ ID NO 4
<211> LENGTH: 76
<212> TYPE: PRT
<213> ORGANISM: Babesia microti

<400> SEQUENCE: 4
```

Met Ala Asn Glu Val Lys Gly Ala Ile Glu Glu Val Asn Lys Ile Ile
1               5                   10                  15

Asp Val Leu Val Ser Asn Ile Arg Asp Ser Gly Tyr Val Ile Asp Asn
            20                  25                  30

Tyr Ile Ile Ser Ser Phe Lys Ser Val Leu Ser Ile Ile Asn Lys Ile
        35                  40                  45

Ala Gln Asn Thr Asn Val Ser Asn Val Ile Ile Pro Gly Leu Lys Ala
    50                  55                  60

Leu Thr Leu Ser Val Phe Leu Ile Leu Thr Ile Ala
65                  70                  75

```
<210> SEQ ID NO 5
<211> LENGTH: 27
<212> TYPE: DNA
<213> ORGANISM: Artificial
<220> FEATURE:
<223> OTHER INFORMATION: Primer

<400> SEQUENCE: 5
gacgacgaca agagcctgac tatcggg                                        27

<210> SEQ ID NO 6
<211> LENGTH: 28
<212> TYPE: DNA
<213> ORGANISM: Artificial
<220> FEATURE:
<223> OTHER INFORMATION: Primer

<400> SEQUENCE: 6
gaggagaagc ccggctataa gctgtaag                                       28

<210> SEQ ID NO 7
<211> LENGTH: 30
<212> TYPE: DNA
<213> ORGANISM: Artificial
<220> FEATURE:
<223> OTHER INFORMATION: Primer

<400> SEQUENCE: 7
gacgacgaca agagggatgg cgattataac                                     30

<210> SEQ ID NO 8
<211> LENGTH: 25
<212> TYPE: DNA
<213> ORGANISM: Artificial
<220> FEATURE:
<223> OTHER INFORMATION: Primer

<400> SEQUENCE: 8
gaggagaagc ccggggtac tatat                                           25
```

BABESIA MICROTI GENOMIC CLONES CONTAINING NOVEL ANTIGENS USEFUL IN THE DIAGNOSIS OF BABESIOSIS

CROSS-REFERENCE TO RELATED APPLICATIONS

The present application is a divisional of U.S. Ser. No. 12/386,097, filed Apr. 14, 2009, which claims the benefit of priority under 35 U.S.C. §119(e) to U.S. Provisional Application Nos. 61/124,093 filed Apr. 14, 2008, 61/124,296 filed Apr. 14, 2008, and 61/196,327 filed Oct. 16, 2008, the entire contents of each of the above-referenced patent applications are hereby incorporated by reference in their entireties.

FIELD OF THE INVENTION

The present invention generally relates to a genomic clone containing a gene that encodes a bacterial antigen. Specifically, the present invention is directed to novel genes encoding antigens in *Babesia microti*. These antigens are useful in the detection of babesiosis, such as ELISA.

BACKGROUND OF THE INVENTION

*Babesia microti* is an apicomplexan intraerythrocytic parasite that is the etiological agent of babesiosis. The host for *Babesia microti* is the white footed mouse, *Peromyscus leucopus*, although other small rodents are also susceptible to infection (Horner et al., 2000). The parasite is transmitted by the bite of a deer tick, *Ixodes scapularis*, which is endemic to the northeastern section of the United States (Anderson et al., 1991). *Babesia* spp. exists worldwide and *Babesia microti* is the most common cause of babesial infections in the United States. Babesiosis has been increasing in prevalence over the past thirty years and is an emergent zoonotic pathogen (Telford et al., 2004) that has increased concerns to the healthcare and diagnostic industries.

*Babesia microti* infection causes a malaria-like disease including malaise, chills, anemia, fatigue, fever and myalgia. Parasitemia levels appear to correlate with the severity of the disease. While the disease is frequently asymptomatic in healthy individuals, it is most severe in immuno-compromised patients. The time from disease transmission to manifestation ranges from one to six weeks or longer. Proper diagnosis of *Babesia* infection is necessary for the treatment of the disease.

Diagnosis of babesiosis is assessed by several different diagnostic methods including thin blood smear, PCR or serology (Persing et al., 1992; Krause et al., 1994). Blood smear detection is a specific method. Some patients may have a low parasitemia and thus can easily be missed in a smear. Thus, the screening method often yields false negatives. Molecular testing such as polymerase chain reaction (PCR) is a specific test with reported higher sensitivity. However, like blood smear, PCR can only detect current infections, and both of these tests cannot detect *Babesia* infections that have been recently cleared by the host immune system.

Serological diagnostic assay is a specific diagnostic test that can provide evidence for both recent and past infections by determining the antibody response. Current commercial serology tests involve the use of indirect immunofluorescent antibody assay (IFA). This assay is sensitive and specific, but is non-quantitative. It requires expensive fluorescent microscopy to read. In addition, the assay is subjective due to its dependence on the individuals who read the slides. IFA results are reported as titers relative to control samples.

Several groups have reported the identification of various *Babesia* proteins and genes that are speculated to encode immunogenic proteins. U.S. Pat. No. 4,596,707 discloses a soluble *Babesia* antigen isolated from *Babesia*-infected erythrocytes, with a MW of about 900,000. U.S. Pat. No. 5,209,929 discloses three substantially purified *Babesia bigemina* proteins having MWs of ~58,000 Da, ~55,000 Da and ~45,000 Da. U.S. Pat. No. 5,273,884 discloses an antigen (W11C5) with a MW ~160 kDa isolated from *Babesia bovis*. Using a peptide-based approach, U.S. Pat. No. 7,390,626 discloses an ELISA in detecting *Babesia microti, Babsia bovie*, and *Babesia equi*.

U.S. Pat. No. 6,183,976 discloses a family of antigen isolated from *Babesia microti*. Using sonication to randomly shear genomic DNA isolated from infected hamster, a *Babesia microti* genomic expression library. *Babesia microti*-infected patient sera were used to screen for immuno-reactive positive clones. Seventeen antigens, referred to as BMN1-17, were reported. Nine of the isolated antigens belong to partial clones of BMN1-3, and contain a degenerate repeat of six amino acids. Another five antigens bear some homology to each other and contain a degenerate repeat of 32 amino acids. However, the sensitivity and specificity data relating ELISA on these antigens are not reported.

Ryan et al. (2001) describe the development of a Western blot in the diagnosis of recent and current infection with *Babesia microti*. This assay requires the presence of two or more bands to be considered positive and is reported to have high sensitivity and specificity. However, the Western blot assay is not commercially available, in part because the assay is tedious and time-consuming. However, to date, no assay has been developed commercially for the diagnostic use stemming from these studies.

There is a continuing need for a highly sensitive and specific serological assay for the detection of an antibody response for *Babesia microti*. The prior art methods have failed to solve a major goal in the diagnostics industry for this disorder for the past several decades.

SUMMARY OF THE INVENTION

The present invention provides the identification of babesial proteins that can be used as the solid phase of an ELISA assay for accurately and quantitatively determining sero-positivity to indicate current or recent infection with *Babesia microti*.

In one aspect, the present invention provides two (2) novel antigens from *Babesia microti* isolated from a genomic library screen (namely, 5-1-1 and 0-1-1 76). These antigens are useful in the development of diagnostic ELISA for both IgG and IgM to identify patients who are sero-positive for *Babesia microti* infection.

The present inventors have cured the prior art methods and successfully identified immuno-reactive *Babesia* proteins that are useful for antibody detection. A genomic DNA expression library was constructed using EcoRI digested *Babesia microti* genomic DNA, and then screened with pooled *Babesia*-positive human sera. The present inventors have isolated two genomic DNA clones that encode novel peptides distantly related to the *Babesia microti* seroreactive (BMN) antigen family. The present invention provides in details the cloning, expression, and purification of these antigens as 6×His-tagged fusion proteins, and further demonstrates the use of the two recombinant antigens for the development of IgG and IgM ELISA.

In one aspect, the present invention provides an isolated polypeptide having an amino acid sequence of SEQ ID NO: 2 or SEQ ID NO: 4. In another aspect, the present invention provides a composition containing the isolated polypeptides of SEQ ID:2 or SEQ ID No:4 and a support. The support is polyethylene, polypropylene, glass or a microtiter well.

In one aspect, the present invention provides an isolated polynucleotide having a nucleotide sequence set forth in SEQ ID NO: 1 or SEQ ID NO: 2.

In another aspect, the present invention provides a vector comprising the isolated polynucleotides. The vector comprises a promoter of DNA transcription operably linked to the isolated polynucleotide. Exemplary vectors include pET, pENTR, or pCR®8/GW/TOPO® and exemplary promoters include lac promoter, trp promoter or tac promoter.

In another aspect, the present invention provides a host cell comprising the vector that contains the isolated polynucleotides. Preferably, the host cell is E. coli. Exemplary E. coli includes NovaBlue K12 strain, BL21 (DE3) or BL21 pLyss (DE3).

In a further aspect, the present invention provides a method of producing an isolated polypeptide having an amino acid sequence set forth in SEQ ID NO. 2 or SEQ ID NO: 4, comprising the steps of: (i) introducing an isolated polynucleotide into a host cell, said isolated polynucleotide having nucleotide sequence set forth in SEQ ID NO. 2 or SEQ ID NO: 4; and (ii) growing said host cell in a culture under suitable conditions to permit production of said isolated polypeptide; and (iii) isolating said isolated polypeptide. Preferably, IPTG is added to the culture to induce growth of the host cells.

In yet another aspect, the present invention provides a method of detecting the presence of an antibody against Babesia microti in a biological sample of a mammal, comprising the steps of: (i) immobilizing an isolated polypeptide set forth in SEQ ID No: 2 or SEQ ID NO. 4 onto a surface; (ii) contacting said isolated polypeptide with a patient's biological sample, under conditions that allow formation of an antibody-antigen complex, said biological sample containing either IgG or IgM; and (iii) detecting the formation of said antibody-antigen complex, wherein said detected antibody-antigen complex is indicative of the presence of said antibody against Babesia microti in said biological sample. Preferably, the mammal is a human. Preferably, the antibody is an IgG or IgM. Detection step may include the step of adding an indicator reagent comprising a signal generating compound after step (ii). The indicator reagent may be horseradish peroxidase.

In one aspect, the present invention provides a method of diagnosing an infection of Babesia microti in a mammal, comprising the steps of: (i) obtaining a biological sample from a mammal suspected of having a Babesia microti infection; (ii immobilizing an isolated polypeptide set forth in SEQ ID No: 2 or SEQ ID NO: 4 onto a surface; (iii) contacting said purified polypeptide with said biological sample, under conditions that allow formation of antibody-antigen complex; and (iv) detecting said antibody-antigen complex, wherein said detected antibody-antigen complex is indicative of the presence of said antibody against Babesia microti in said biological sample. Preferably, the contacting step is performed at room temperature for about 1 hour.

In an aspect, the present invention provides an article of manufacture or kit comprising a packaging material; and an isolated polypeptide set forth in SEQ ID No: 2 or SEQ ID NO: 4. Preferably, the package material comprises an instruction for detecting the presence of antibody against Babesia microti.

BRIEF DESCRIPTION OF THE DRAWINGS

FIG. 2 depicts the nucleotide sequence of 5-1-1 (SEQ ID NO:1). The 372 bp genomic DNA clone 5-1-1 encodes an open reading frame of 124 amino acids.

FIG. 3 depicts the deduced amino sequence of ORF encoding antigen 5-1-1 (SEQ ID NO: 2). The largest open reading frame encoded within clone 5-1-1 is an ORF of 124 amino acids.

FIG. 4 depicts the BLAST analysis of antigen 5-1-1 showing its identity with BMN1-2, a previously reported member of the sero-reactive antigen family in Babesia. The 124 amino acid ORF of antigen 5-1-1 is 61%-63% identical to four members of the sero-reactive antigen family (BMNs) identified by Lodes (Lodes et al., 2000).

Figure 6:
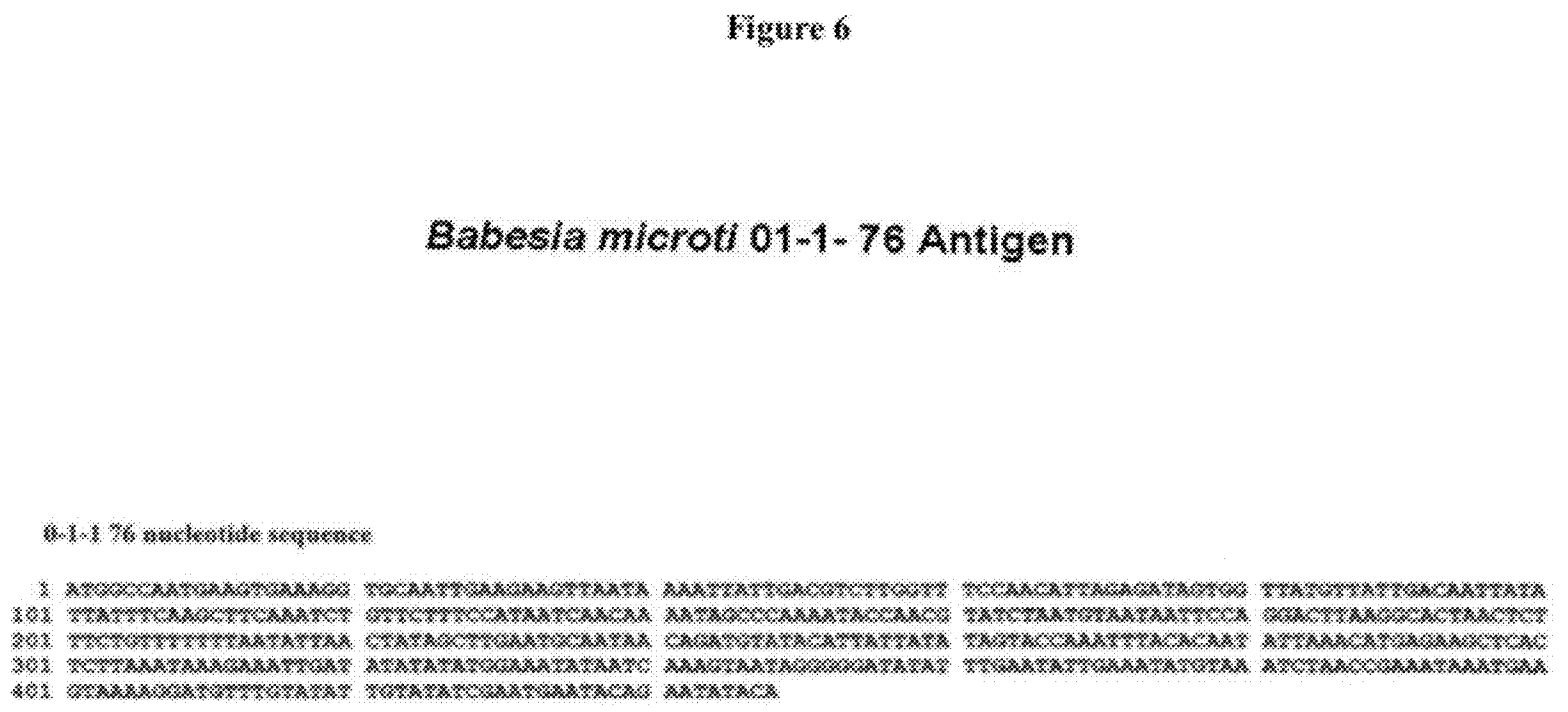

FIG. 6 depicts the nucleotide sequence of 0-1-1 76 (SEQ ID NO:3). The 448 bp genomic DNA clone 0-1-1 76 encodes an open reading frame of 76 amino acids.

FIG. 7 depicts the deduced amino sequence of partial ORF encoding antigen 0-1-176 (SEQ ID NO: 4). The largest open reading frame encoded within clone 0-1-1 76 is an ORF of 76 amino acids.

FIG. 8 depicts the BLAST analysis of antigen 0-1-1 76. The 76 amino acid ORF of antigen 0-1-1 76 is 55% identical to sero-reactive antigen BMN1-3.

FIG. 9 depicts the phylogram depicting the relationships between 5-1-1 and 0-1-1 76 protein sequences and sequences of BMN1-2 family of sero-reactive antigens. Clones 5-1-1 and 0-1-1 76 were identified from a Babesia microti genomic DNA expression library screened with Babesia microti IFA-positive human sera.

FIG. 10 depicts the Coomassie blue stained 15% SDS-PAGE gel analysis of purified proteins O-1-1 76 and 5-1-1.

FIG. 14 depicts the IgM ELISA results of an IgM capture test using antigen 5-1-1 for detection. IFA-positive (n=21) samples are represented as ♦ while IFA-negative (n=27) samples are represented as ■. Index values<0.9 are reported as negative, those between 0.9 and 1.1 are reported as equivocal and results>1.1 are reported as positive.

DETAILED DESCRIPTION OF THE INVENTION

Figure 1:
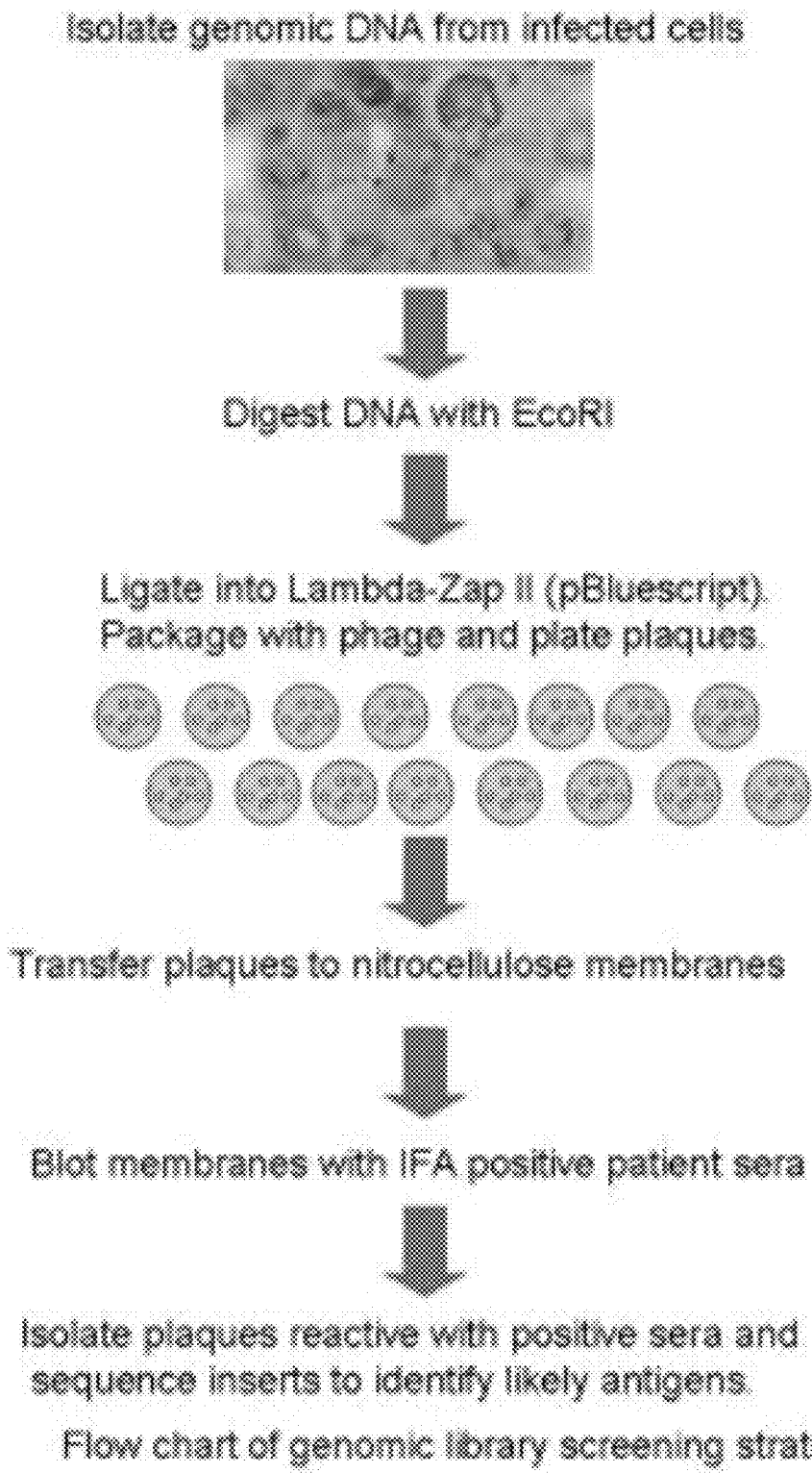
FIG. 1 depicts the flow chart for genomic library screening strategy.

The present invention can be better understood from the following description of preferred embodiments, taken in conjunction with the accompanying drawings. It should be apparent to those skilled in the art that the described embodiments of the present invention provided herein are merely exemplary and illustrative and not limiting. Numerous embodiments of the modifications thereof are contemplated as falling within the scope of the present invention and equivalents thereto. All publications, patent applications, patents, and other references mentioned herein are incorporated by reference in their entirety.

As used herein, the term "5-1-1" refers to a polypeptide having an amino acid sequence as set forth in SEQ ID NO: 2 (See, FIG. 3). The polypeptide represents the 5-1-1 protein in *Babesia microti*. The 5-1-1 polypeptide is shown by the present inventors to bind to antibodies that are present in *Babesia* patients' sera in an ELISA assay.

As used herein, 5-1-1 gene in *Babesia microti* has a nucleotide sequence as set forth in SEQ ID NO: 1 (Accession No. 50649.1).

As used herein, the term "0-1-1 76" refers to a polypeptide having an amino acid sequence as set forth in SEQ ID NO: 4. The polypeptide represents the 0-1-1 76 protein in *Babesia microti*. The 0-1-1 76 polypeptide is shown by the present inventors to bind to antibodies that are present in *Babesia* patients' sera in an ELISA assay.

As used herein, 0-1-1 76 gene in *Babesia microti* has a nucleotide sequence as set forth in SEQ ID NO: 3 (Accession No. 50650).

As used herein, the term "isolated" (when used in the context of polypeptides and nucleic acids) means that the polypeptides or nucleic acids are essentially free of other substances with which they may be found in vivo. In particular, the polypeptides or nucleic acid are substantially pure so as to be useful in, for example, generating antibodies, expression or producing pharmaceutical preparations.

As used herein, the term "control sequence" refers to DNA sequences necessary for the expression of an operably linked coding sequence in a host micro-organism. The control sequences that are suitable for prokaryotes, for example, include a promoter, optionally an operator sequence, and a ribosome-binding site. Eukaryotic cells are known to utilize promoters, polyadenylation signals, and enhancers.

As used herein, the term "host cell" refers to a cell containing a vector and supports the replication and expression of the vector. Host cells may be prokaryotic cells such as *E. coli* or eukaryotic cells such as yeast, or mammalian cells. Preferably, host cell is *E. coli*.

As used herein, the term "introduced" refers to inserting a nucleic acid into a cell, which encompasses "transfection," "transformation," or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

As used herein, the term "ELISA" refers to "Enzyme-Linked ImmunoSorbent Assay" and is a biochemical technique used in detecting the presence of antibody or antigen in a sample.

As used herein, the term "IFA" refers to immunofluorescence assay. "IFA sero-positive sera from a patient" refers to sera (obtained from a patient) that exhibit positive immunofluorescence staining towards cells that have been infected with *Babesia microti*. "IFA sero-negative sera from a patient" refers to sera (obtained from a patient) that exhibit negligible immunofluorescence staining towards cells that have been infected with *Babesia microti*.

As used herein, the terms "polypeptide," "peptide," or "protein" are used interchangeably.

As used herein, the term "recombinant polypeptide" refers to a polypeptide that is recombinantly expressed by a host cell via the use of a vector that has been modified by the introduction of a heterologous nucleic acid. As used herein, the "synthetic polypeptide" refers to a polypeptide that is synthesized chemically (not a naturally occurring polypeptide). For purposes of the present invention, these polypeptides are intended to encompass polypeptide variations so long as they still possess the ability to bind to antibodies present in *Babesia* infected patients in an ELISA assay. One of an ordinary skill in the art would appreciate that the amino acid sequence variations of these polypeptides may include (i) conservative substitutions, (ii) substitution, (iii) addition, and (iv) deletion of amino acids. It would be further appreciated that a polypeptide variant having a sufficiently high % amino acid sequence identity (e.g., >90%) is intended to be encompassed by the present invention, provided that the polypeptide maintains its antibody binding ability.

As used herein, the term "% amino acid sequence identity" is defined as the percentage of amino acid residues that are identical to the amino acid residues in the *Babesia* antigen polypeptide. Alignment for purposes of determining percent amino acid sequence identity can be achieved in various ways that are well within the skill in the art, for instance, using publicly available computer software such as BLAST, BLAST-2, ALIGN or Megalign (DNASTAR) software.

As used herein, the term "recombinant" includes reference to a cell or vector that has been modified by the introduction of a heterologous nucleic acid or that the cell is derived from a cell so modified.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium, or just a single time per host as the host reproduces by mitosis. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells that have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

As used herein, the term "mammal" refers to any vertebrate of the class mammalia, having the body more or less covered with hair, nourishing the young with milk from the mammary glands, and, with the exception of the egg-laying monotremes, giving birth to live young. Preferably, the mammal is human.

As used herein, the term "primer" refers to a nucleotide sequence which can be extended by template-directed polymerization. For the purpose of this application, the term "nucleotide sequence" is intended to include DNA or modification thereof.

As used herein, the term "biological sample" may include but are not limited to blood (e.g., whole blood, plasma, serum, etc), cerebrospinal fluid, synovial fluid, and the like from a mammal such as a human or domestic animal. Extraction of nucleic acids from biological samples is known to those of skill in the art.

There is disclosed herein the genomic cloning, expression, and purification of two novel antigens from the tick-borne pathogen *Babesia microti*. The present invention provides that these antigens are distantly related to a family of sero-reactive antigens previously reported by Lodes et al. (2000). Using an expression library of randomly sheared genomic DNA, Lodes et al. has reported the identification of 17 *Babesia microti* antigens. It is noteworthy that the antigens disclosed in the present study were different from that disclosed by the Lodes group. This might be related, in part, to the differences in the methodology used to construct the genomic DNA libraries used in these studies.

In this application, the present inventors used a *Babesia* genomic DNA library that was constructed with DNA digested with EcoRI (See, FIG. 1). Not wishing to be bound by a theory, it is speculated that the random shearing of genomic DNA (as used in Lodes et al.) would be more disruptive to cross-reactive epitopes than the digestion of DNA with EcoRI restriction enzyme (as used in this application). This is likely if the target genomic DNA digested with EcoRI was A-T rich, where the number of expected restriction fragments would be relatively low in comparison to the number of fragments expected from the random shearing approach taken by Lodes et al.

Because *Babesia microti* genome sequence has not been published, the GC/AT content of this organism is unknown. The nucleotide sequence of one antigen identified by Lodes (e.g., BMN1-3) is 72% A-T, which is consistent with our observation, and supports this hypothesis.

There has been no information available to the subcellular localization of antigens 5-1-1 and 01-1 76 present in the pathogen. Without wishing to be bound by a theory, it is possible, using monoclonal antibodies against these proteins, that the 5-1-1 and 0-1-1 76 antigens may not co-localize with any of the BMN proteins, and thus represent a new class of sero-reactive antigens.

In accordance with the present invention, there is disclosed the use of at least one of these antigens (e.g., 5-1-1) to distinguish *Babesia* sero-positive from sero-negative patients. As epidemiological surveys have shown that seropositivity with *Babesia microti* is prevalent in the murine population in endemic areas (Anderson et al., 1991), proper diagnosis relying on laboratory findings has become of greater importance. In a survey of blood donors in nonendemic and endemic regions of Connecticut it was shown that the seroprevalence was 0.3% in nonendemic areas compared to 1.4% in endemic regions (Lieby et al., 2005). In addition, as the *Babesia* parasite is carried and transmitted by the same species of tick, *Ixodes scapularis*, responsible for other common tick-borne illnesses including, *Borrelia, Ehrlichia* and *Rickettsia*, the identification of patients with multiple concurrent infections is highly relevant.

Co-infection with *Bartonella burgdorferi* and *Babesia microti* may account for subsets of Lyme disease cases which have aberrant or difficult to treat symptoms. Sero-surveys have estimated that as many as 13% of Lyme disease patients in *Babesia* endemic areas are coinfected with *Babesia microti* and the same is seen in the murine population. In addition, there are other pathogens carried by these ticks including *Anaplasma phagocytophilum* and *Bartonella henselae* that may also be co-transmitted to the host indicating that further study into the consequence of simultaneously acquiring multiple pathogens is warranted.

In accordance with the present invention, there is disclosed the identification of two novel genomic clones isolated from the screening of a *Babesia microti* genomic DNA expression library.

In accordance with the present invention, there is disclosed the clone 5-1-1 which is a 372 bp DNA insert (FIG. 1; SEQ ID NO: 1) (Accession No. FJ440563) encoding a 124 amino acid peptide (FIG. 1; SEQ ID NO: 2) (Accession No: ACL50649).

In accordance with the present invention, there is disclosed the clone 0-1-1 76 which is a 448 bp DNA insert (FIG. 2; SEQ ID NO:3) (Accession No: FJ440564) encoding a 76 amino acid peptide (FIG. 2; SEQ ID NO:4) (Accession No: ACL50650).

Sequence and BLAST analysis of the clone 5-1-1 reveals 63% identity to three members of the sero-reactive antigen family reported by Lodes (2000). ClustalW analysis of clone 5-1-1 with these antigens and BMN1-6 (61% identity to 5-1-1) shows that the 5-1-1 amino acid sequence is divergent in regions highly conserved between BMN family members of this family (FIG. 5).

Blast analysis of the clone 0-1-1 76 reveals 55% with the sero-reactive antigen BMN1-3 (FIG. 8). These data are consistent with the notion that 5-1-1 and 0-1-1 76 are divergent members of the sero-reactive protein family described by Lodes (2000), and suggest that they belong to a new, previously unidentified protein family. FIG. 9 shows the phylogentic relationship among the protein sequence of seven members of the BMN family and the 5-1-1 and 0-1-1 76 antigen.

WA1 is a pathogenic *Babesia* species that is similar to *Babesia microti*. WA1 has been shown to have little cross-reactivity with *Babesia microti* when assessed by IFA (Quick et al., 1993), but its cross reactivity with 5-1-1 is unknown. The cross reactivity of 5-1-1 with other babesial species such as *Babesia divergens* is also unknown. It remains to be determined if this antigen can distinguish between *Babesia microti* which is common in the northeastern United States and other babesial species which are common in other geographic regions.

Recombinant Expression of Clones 5-1-1 and 0-1-1 76: Vectors and Hosts

In one embodiment, the present invention provides the expression of the DNA sequences disclosed herein. As is well known in the art, DNA sequences may be expressed by operatively linking them to an expression control sequence in an appropriate expression vector and employing that expression vector to transform an appropriate unicellular host. Such operative linking of a DNA sequence of this invention to an expression control sequence, of course, includes, if not already part of the DNA sequence, the provision of an initiation codon, ATG, in the correct reading frame upstream of the DNA sequence. A wide variety of host/expression vector combinations may be employed in expressing the DNA sequences of this invention. Useful expression vectors, for example, may consist of segments of chromosomal, non-chromosomal and Synthetic DNA sequences.

In accordance with the present invention, a vector may be, for example, a plasmid vector, a single or double-stranded phage vector, a single or double-stranded RNA or DNA viral vector. Plasmids disclosed herein are either commercially available, publicly available, or can be constructed from available plasmids by routine application of well-known, published procedures. Many plasmids and other cloning and expression vectors that can be used in accordance with the present invention are well known and readily available to those of skill in the art.

Preferred among vectors, in certain respects, are those for expression of polynucleotides and polypeptides of the present invention. Generally, such vectors comprise cis-acting control regions effective for expression in a host operatively linked to the polynucleotide to be expressed. Generally, any vector suitable to maintain, propagate or express polynucleotides to express a polypeptide in a host may be used for expression in this regard. Appropriate DNA sequence may be inserted into the vector by any of a variety of well-known and routine techniques, such as, for example, those set forth in Sambrook, et al., MOLECULAR CLONING, A LABORATORY MANUAL, 2nd Ed.; Cold Spring Harbor Laboratory Press, Cold Spring Harbor, N.Y. (1989). Vectors for propagation and expression generally will include selectable markers and amplification regions, such as, for example, those set forth in Sambrook et al.

The DNA sequence in the expression vector is operatively linked to appropriate expression control sequence(s), including, for instance, a promoter to direct mRNA transcription. Representatives of such promoters include, but are not limited to, the phage lambda PL promoter, the $E.\ coli$ lac, trp and tac promoters, the SV40 early and late promoters and promoters of retroviral LTRs. Among known prokaryotic promoters suitable for expression of polynucleotides and polypeptides in accordance with the present invention are the $E.\ coli$ LacI and LacZ and promoters, the T3 and T7 promoters, the gpt promoter, the lambda PR, PL promoters and the trp promoter.

Suitable vectors include pET, pENTR, and pCR®8/GW/TOPO® and the like. These vectors are listed solely by way of illustration of the many commercially available and well known vectors that are available to those of skill in the art for use in accordance with this aspect of the present invention. The promoter may contain lac promoter, trp promoter and tac promoter. Transcriptional and translational control sequences are DNA regulatory sequences, such as promoters, enhancers, terminators, and the like, that provide for the expression of a coding sequence in a host cell.

In general, expression constructs will contain sites for transcription initiation and termination, and, in the transcribed region, a ribosome binding site for translation. The coding portion of the mature transcripts expressed by the constructs will include a translation initiating codon, for example, AUG or GUG, at the beginning and a termination codon appropriately positioned at the end of the polypeptide to be translated.

A DNA sequence is "operatively linked" or "operably linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted upstream (5') of and in reading frame with the gene. A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

In one embodiment, a host cell contains the vector comprising the polynucleotides of the present invention. Host cells can be genetically engineered to incorporate polynucleotides and express polypeptides of the present invention. Introduction of a polynucleotides into the host cell can be affected by calcium phosphate transfection, DEAE-dextran mediated transfection, transvection, microinjection, cationic lipid-mediated transfection, electroporation, transduction, infection or other equivalent methods. Such methods are described in many standard laboratory manuals, such as Sambrook, et al., MOLECULAR CLONING: A LABORATORY MANUAL, $2^{nd}$ Ed., Cold Spring Harbor Laboratory Press, Cold Spring Harbor, N.Y. (1989). Exemplary host cell may include bacterial cells such as Staphylococci or $E.\ coli$. Various $E.\ coli$ strains include, for example, NovaBlue strain, BL21 (DE3) or BL21 pLsS (DE3). Other representative examples of appropriate hosts may include mammalian cells such as DHO, COS, HeLa cells and the like.

It will be understood that not all vectors, expression control sequences and hosts will function equally well to express the DNA sequences of this invention. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered. In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products. Considering these and other factors a person skilled in the art will be able to construct a variety of vector/expression control sequence/host combinations that will express the DNA sequences of this invention on fermentation or in large scale animal culture.

Polynucleotide constructs in host cells can be used in a conventional manner to produce the gene product encoded by the recombinant sequence. Alternatively, the polypeptides of the invention may be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., MOLECULAR CLONING: A LABORATORY MANUAL, 2nd Ed., Cold Spring Harbor Laboratory Press, Cold Spring Harbor, N.Y. (1989).

Promoter regions can be selected from any desired gene using vectors that contain a reporter transcription unit lacking a promoter region, such as a chloramphenicol acetyl transferase ("CAT") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available, such as pKK232-8 and pCM7. Promoters for expression of polynucleotides of the present invention include not only well-known and readily available promoters, but also promoters that readily may be obtained by the foregoing technique, using a reporter gene.

After recombinant expression, cells typically are harvested by centrifugation, disrupted by physical or chemical means, and the resulting crude extract retained for further purification. The recombinantly expressed polypeptides of the present invention can be conveniently recovered and purified from recombinant cell cultures by well-known methods including ammonium sulfate or ethanol precipitation, acid extraction, anion or cation exchange chromatography, hydrophobic interaction chromatography, affinity chromatography, and the like. Preferably, high performance liquid chromatography may be employed for purification. Well-known techniques for refolding protein may be employed to regenerate active conformation when the polypeptide is denatured during isolation and or purification.

The present invention provides an improved method for detecting an existing and past infection with the parasite *Babesia microti* than those that have been available previously. As the immuno-compromised and other susceptible populations expand it becomes increasingly important to be able to identify exposure to pathogens such as *Babesia*. Additionally, many individuals show evidence of an infection following a tick bite but are negative for exposure to *Borrelia* which is a more well-known tick borne disease. Accordingly, the present test provides an important tool to the diagnostic arsenal for detecting *Babesia microti* that is available to physicians.

ELISA Assays

Detection of presence of antibodies which specifically bind with *Babesia microti* can be analyzed by an ELISA assay. A *Babesia microti* antigen is first immobilized onto a surface. The surface may be any solid material known to those of ordinary skill in the art to which an antigen may be attached. For example, the solid support may be polyethylene, polypropylene, glass, and the like. Conveniently the solid support of a microtiter well may be used. A biological sample (such as blood, plasma, or serum) is then added to allow immobilization (i.e., bound") to occur. Optimal times and conditions for immobilization can easily be achieved by one of skilled artisan. Typically, contact time may range from about 1 hour to about 1 day. About 100 µg to about 100 ng antigen may be used to immobilize antigens onto a plastic microtiter plate (e.g., polystyrene or polyvinylchloride). Preferably, the antigen is in the amount of about 1 µg.

Antibodies present in the biological sample are allowed to bind with the bound *Babesia microti* antigen. After washing, a secondary antibody bound to a detectable moiety can be added to enhance the detection. ELISA can be readily adapted to accomplish the detection of both *Babesia microti* antigen and antibodies which specifically bind therewith.

IgG ELISA may be performed as follows: (1) immobilizing a *Babesia microti* antigen onto a surface; (2) contacting the bound antigen with a biological sample containing antibodies from a mammal; (3) adding an anti-human IgG antibody that has a detectable moiety (e.g., horseradish peroxidase enzyme); (4) adding a substrate for the enzyme; (5) adding a color reagent. Color change is indicative of the presence of IgG antibodies.

IgM ELISA may be performed using the similar protocol as in IgG ELISA as described above (i.e., immobilizing the recombinant protein onto a surface).

Alternatively, IgM ELISA may also be performed via "antibody capture" as follows: (1) immobilizing an anti-human IgM antibody onto a surface; (2) contacting the bound antibody with a biological sample from a mammal; (3) contacting the above with biotinylated *Babesia microti* antigens (e.g., 5-1-1 or 0-1-1 76); (4) adding strepavidin-horseradish peroxidase; (5) adding a color reagent. Color change is indicative of the presence of IgM antibodies.

In one embodiment, IgM capture ELISA is provided. Specifically, flat-bottomed 96-well polystyrene plates are coated with goat anti-human IgM antibody, followed by serial two-fold dilutions of sera including 5 negative controls, biotinylated *Babesia microti* or negative control antigens, and strepavidin-horseradish peroxidase goat and the substrate (TMB). Between each step, plates are incubated for 1 hour at 37° C., and then washed 3 times with 0.05% Tween 20 in phosphate buffered-saline (pH 7.4). Dilutions of sera are considered positive when the difference in absorbance between that serum specimen when tested with *Babesia microti* antigen and the negative control antigen exceeds the means plus 3 standard deviations of the 5 negative control sera tested with both *Babesia microti* and negative control antigens. Both the IgG and IgM ELISA assays are effective for the diagnosis of babesiosis.

The following examples are provided to further illustrate various preferred embodiments and techniques of the invention. It should be understood, however, that these examples do not limit the scope of the invention described in the claims. Many variations and modifications are intended to be encompassed in this application.

EXPERIMENTAL STUDIES

Example 1

Identification of *Babesia* Antigens Cross-Reactive with *Babesia*-Positive Human Sera I. Construction of Genomic Library Genomic DNA was isolated from infected hamster blood using Qiamp DNA blood kit (Qiagen, Valencia, Calif.). The isolated genomic DNA was digested with EcoRI and precipitated. (FIG. 1). 150 ng of digested genomic DNA was ligated into the pBluescript SK(−) vector (Stratagene, La Jolla, Calif.). The ligation reaction was packaged with phage Gigapack III (Stratagene, La Jolla, Calif.), and then titered to determine the ideal screening density.

II. Screening of Genomic Library

The *Babesia* library was plated onto 20 NZY agar plates in *E. coli* strain XL-1 Blue MRF-, and plaques were allowed to form for 8 hours. Nitrocellulose membranes were soaked for 15 minutes in 100 mM IPTG and plaques were transferred to the membranes by incubation at 37° C. for 3 hours. The membranes were washed in PBS-Tween 20 and blocked overnight in 1% BSA (Bovine Serum Albumin) in PBS (Phosphate Buffered Saline).

Positive plaques were identified by immunoblotting with pooled positive sera obtained from an IFA-positive control (Fuller Laboratories, Fullerton, Calif.) at a final dilution of 1:500. Positives were detected using anti-human IgG conjugated to HRP (Horse Radish Peroxidase) (KPL, Gaithersburg, Md.) secondary antibody at a dilution of 1:2000 and developed with DAB substrate. Following the addition of 30 μl hydrogen peroxide, the solution was used to visualize the positive spots on the membranes corresponding to plaques expressing antigenic proteins. Positive plaques were excised from the agar and placed into SM buffer with chloroform. They were then re-plated at a lower density using the same pool of positive sera in a mixture of XLOLR and XPORT *E. coli* strains and 704 helper phage, and then re-screened with the positive sera to obtain a homogeneous plasmid population.

Positive plaques were identified and grown in overnight cultures for plasmid DNA isolation. Screening of the library resulted in multiple positive clones from which plasmid DNA was isolated. Plasmid DNA was digested to confirm single inserts and then sequenced. Sequence information was used to identify likely antigenic candidates based on homology of the peptides with other members of the plasmodia family.

Example 2

Two Novel Genomic Clones

Sequencing of these clones revealed multiple inserts containing open reading frames (ORFs) with homology to known *B. microti* genes, as well as ORFs with homology to other Apicomplexan parasites such as *Theilleria* and *Plasmodium* species. Three ORFs were chosen for further analysis by protein expression, two from insert O-1-1, and one from insert 5-1-1.

Based on preliminary experiments with the two ORFs from clone O-1-1, one was chosen for further study based on its reactivity to IFA-positive and IFA-negative patient sera (data not shown). O-1-1 76 is a 76 amino acid (aa) sequence encoding an 8.2 kDa protein (FIG. 7). 5-1-1 is a 124 aa, 14.8 kDa partial protein (FIG. 3). The library insert for clone 5-1-1 did not appear to contain the full-length protein as there was no discernable stop codon in the insert.

Example 3

Protein Production

Primers were designed to clone O-1-1 76 and 5-1-1 into the pET30 Ek/LIC (enterokinase ligation-independent cloning) expression vector (Novagen, San Diego, Calif.). A stop codon was engineered into the reverse primer for 5-1-1 to stop protein translation at the end of the insert sequence. For cloning of 5-1-1, forward primer 5'-gacgacgacaagagcctgactatcggg-3' (SEQ ID NO: 5) and reverse primer 5'-gaggagaagcccggctataagctgtaag-3' (SEQ ID NO: 6) were used to amplify the clone before ligation into pET30Ek/LIC expression vector. For the 0-1-1 76 cloning, forward primer 5'-gacgacgacaagagggatggcgattataac-3' (SEQ ID NO: 7) and reverse primer 5'-gaggagaagcccgggggtactatat-3' (SEQ ID NO: 8) were used prior to ligation into pET vector.

Protein expression in transformed BL21 *E. coli* was induced using the Overnight Express Autoinduction System (Novagen, San Diego, Calif.).

Expressed protein was purified over a nickel column (Ni-NTA column) (Novagen, San Diego, Calif.) using the N-terminal His-tag on the expressed proteins as provided by the pET-30 Ek-LIC vector. The eluted protein was concentrated and stored for use.

Figure 4:
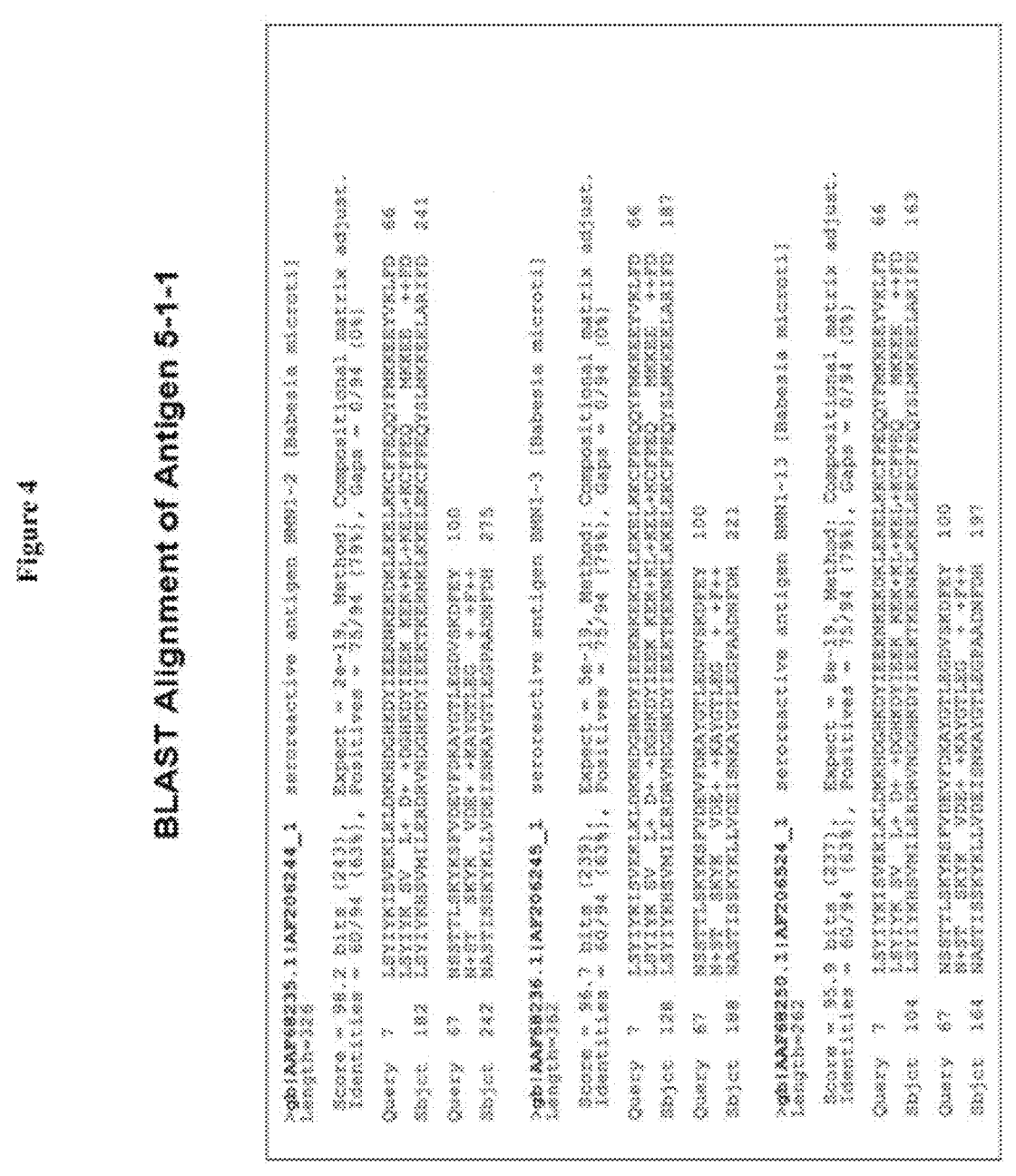

O-1-1 76 was purified under native conditions using 250 mM imidizole for elution from the column. 5-1-1, however, was purified under denaturing conditions using a pH gradient in 8M Urea because the protein was sequestered in the inclusion body pellet of the *E. coli* culture. Coomassie blue stained elutions of both O-1-1 76 and 5-1-1 are presented in FIG. 4A.

Example 4

Immunodetection of Antigens 5-1-1 and 0-1-1 76

Purified protein was run on a 15% SDS-PAGE gel (FIG. 10). The protein was transferred onto PVDF membrane, followed by blocking in 1% BSA for 1 hour at room temperature. Primary antibody (positive or negative sera) was diluted 1:250 in 1% BSA, and incubated for 90 minutes at room temperature. Antigen specific antibodies were detected by goat anti-human IgG-Alkaline Phosphatase (Southern Biotech, Birmingham Ala.) at a dilution of 1:3,000, followed by detection with NBT/BCIP (Moss, Pasadena Md.).

Figure 11:
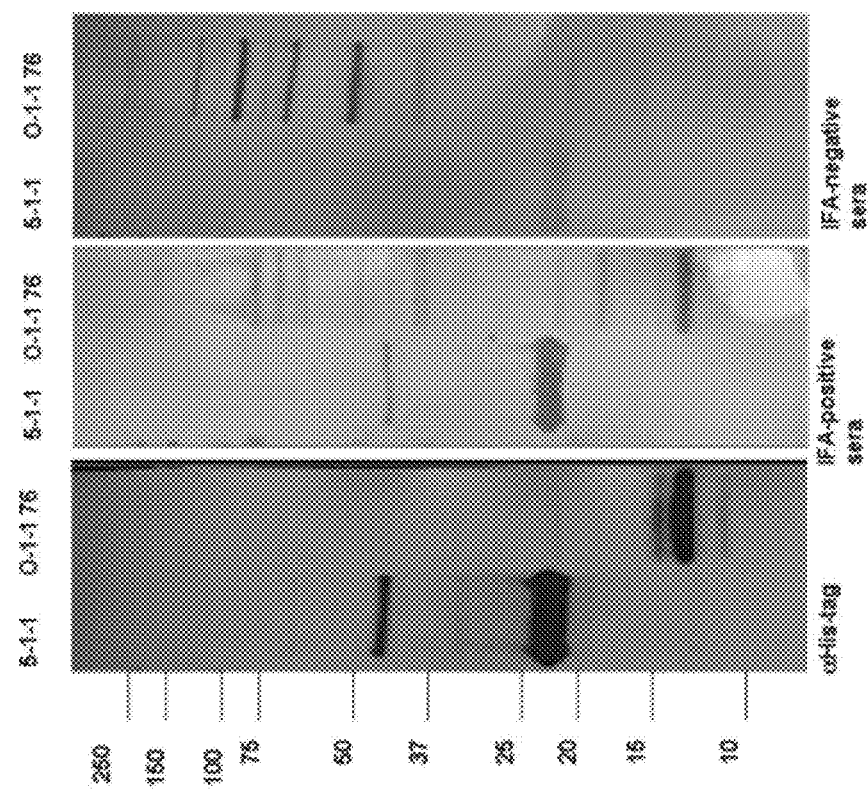
FIG. 11 depicts the Western blot analysis of proteins O-1-1 76 and 5-1-1, First panel utilized a monoclonal antibody to the His-tag, second panel is an IFA positive sera sample and the third panel is an IFA negative sera sample. Molecular weight marker used was Precision Plus all-blue (BioRad).

Western blotting was performed using a His-tag monoclonal antibody, one IFA positive patient sera and one IFA negative patient sera (FIG. 11). O-1-1 76 exhibited some background reactivity with the IFA-negative sera although the reactive bands are all of different sizes than the purified protein (FIG. 11). 5-1-1 displayed very little background reactivity and appeared to be more pure than O-1-1 76 (FIG. 11).

Example 5

Characterization of Two Novel *Babesia* Antigens, 5-1-1 and 01-1 76 Distantly Related to the BMN Seroreactive Protein Family We have identified two novel genomic clones isolated from the screening of a *Babesia microti* genomic DNA expression library.

I. Clone 5-1-1

Clone 5-1-1 is a 372 bp DNA insert (FIG. 2) encoding a 124 amino acid peptide (FIG. 3) determined by BLAST analysis to be 63% identical to three members of the sero-reactive antigen family reported by Lodes (2000), BMN1-2, BMN1-3, and BMN1-13 (FIG. 4).

ClustalW analysis of 5-1-1 with these antigens and BMN1-6 (61% identity to 5-1-1) shows that the 5-1-1 amino acid sequence is divergent in regions highly conserved between the BMN family members (FIG. 5). Based on the degree of similarity with these sero-reactive antigens, it is concluded that 5-1-1 is either a novel member of this family or is a member of a new previously unidentified protein family.

II. Clone 0-1-1 76

Clone 0-1-1 76 is a 448 bp DNA insert (FIG. 6) encoding a 76 amino acid peptide (FIG. 7). The highest degree of identity obtained with BLAST analysis is 55% with the sero-reactive antigen BMN1-3 (FIG. 8). These data suggest that 5-1-1 and 01-1 76 are divergent members of the sero-reactive protein family described by Lodes (2000), or belong to a novel protein family.

Example 6

Phylogenetic Study

We conducted a phylogenetic study of the 5-1-1 and 0-1-1 76 and the BMN Protein Family. FIG. 9 shows the phylogenetic relationships among the protein sequences of seven members of the BMN family and the antigens described in this application. As reported in the Lodes paper, the sequences of these seven proteins show a high degree of homology with each other, and these proteins group closely together on the phylogram tree. Based on the similarity of these proteins, they were collectively grouped by these authors into the BMN1-2 family. Based upon amino acid sequences, they appear to be only distantly related to 5-1-1, and show an even greater divergence from 0-1-1 76 (FIG. 9).

Figure 5:
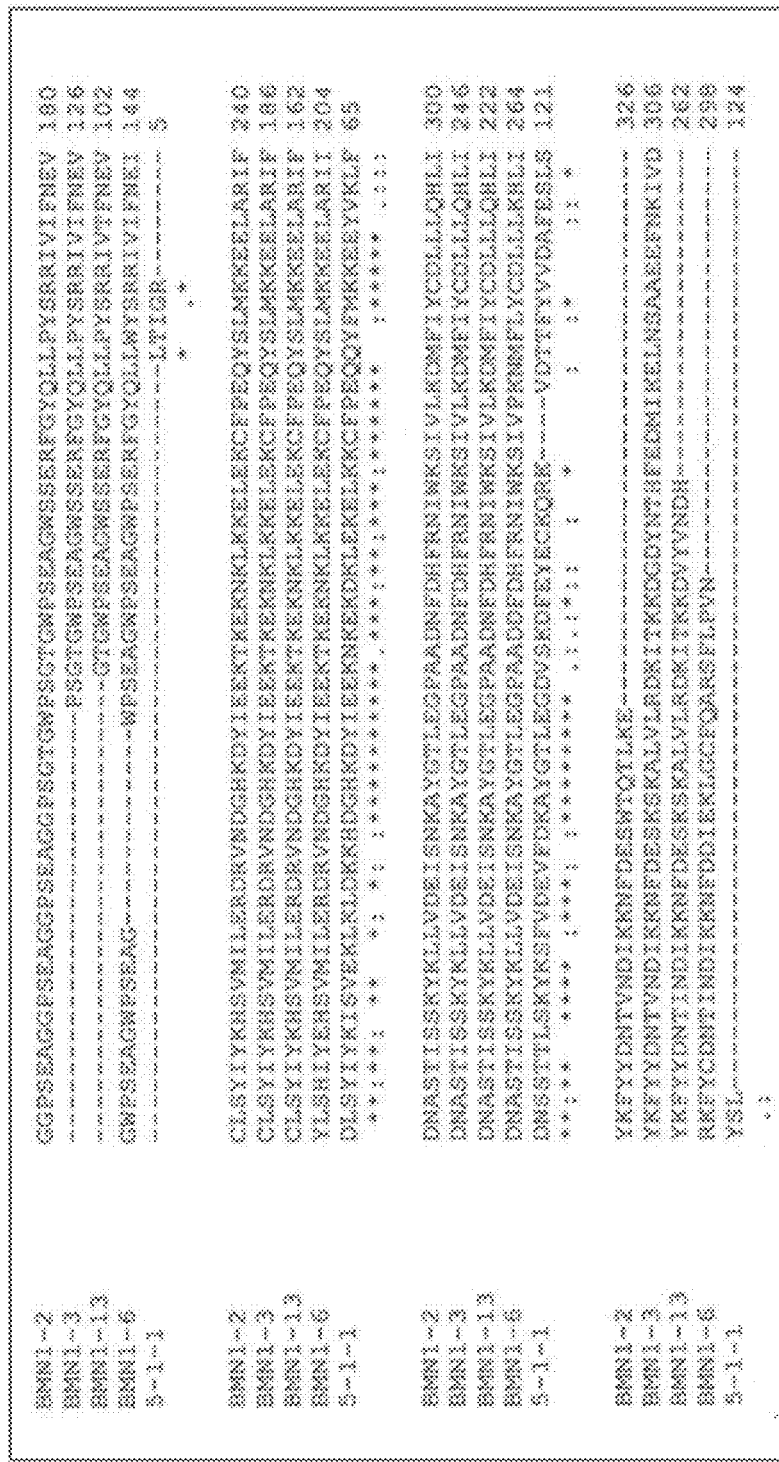
FIG. 5 depicts the ClustalW alignment of the 5-1-1 ORF with the amino acid sequences of four members of the BMN family. The amino acid sequence of antigen 5-1-1 diverges from the BMN family in regions that are highly conserved between members of the BMN family.

BLAST analysis shows a 61% homology of 5-1-1 with BMN1-6 (FIG. 5). We conclude that 5-1-1 is either a newly identified sero-reactive protein, or a distant member of at least the seven members of the BMN protein family.

BLAST analysis shows a 55% homology of 0-1-1 76 with BMN1-2 (FIG. 8). Thus, our phylogenetic analysis suggests that 01-1 76 is either a newly identified protein or a distant member to the other members of the BMN protein family.

Example 7

Development of Enzyme-Linked Immunosorbent Assays for Detection of IgG and IgM

ELISA assays were performed using O-1-1 76 or 5-1-1 as the coating antigen. In these assays, either O-1-1 76 or 5-1-1 was coated onto 96 well plates at 1 µg/ml. Patient sera was reacted to the plates and detected with an alkaline phosphatase conjugate. Both proteins were able to distinguish IFA-positive from IFA-negative patient samples, however the distinction with O-1-1 76 was not significant.

5-1-1 was able to show a significant difference between IFA positive and IFA negative samples (FIG. 12), and this protein was used to continue assay development.

Figure 12:
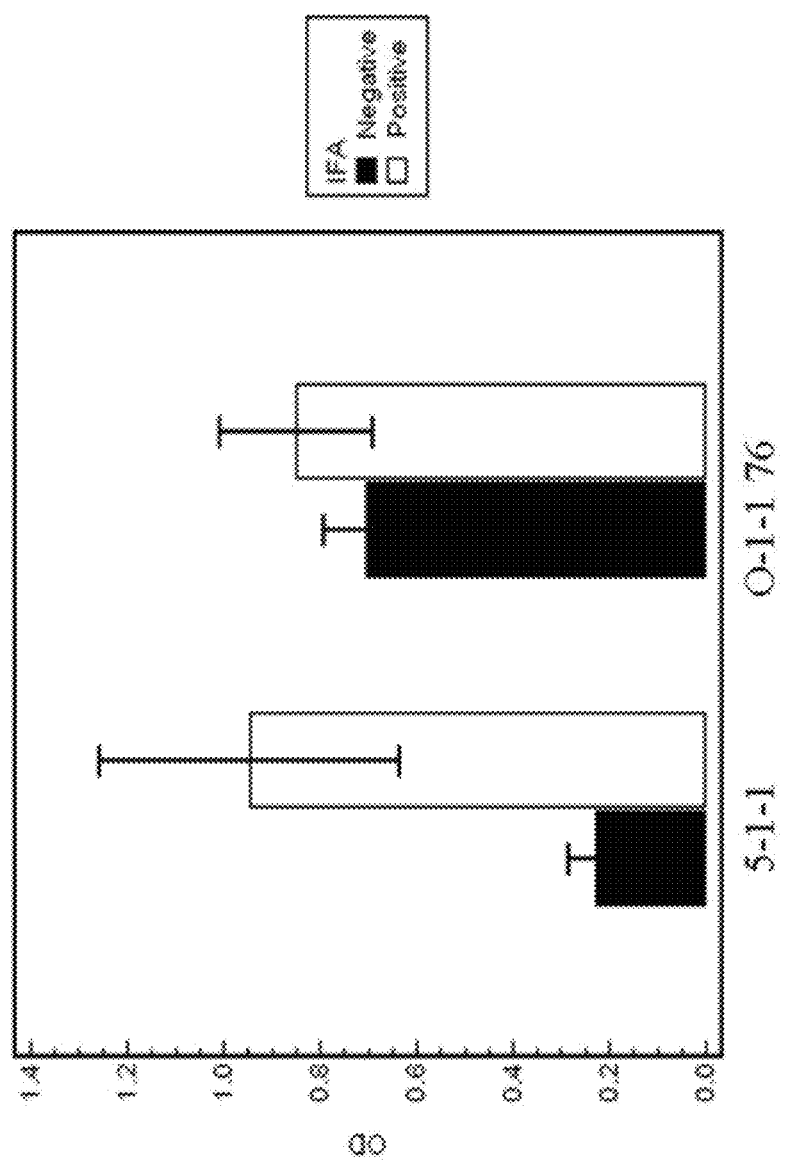
FIG. 12 depicts the IgG ELISA results demonstrating the ability of proteins O-1-1 76 and 5-1-1 to distinguish IFA positive (n=20) from IFA negative (n=27) sera. Error bars indicate 95% confidence intervals.
Figure 13:
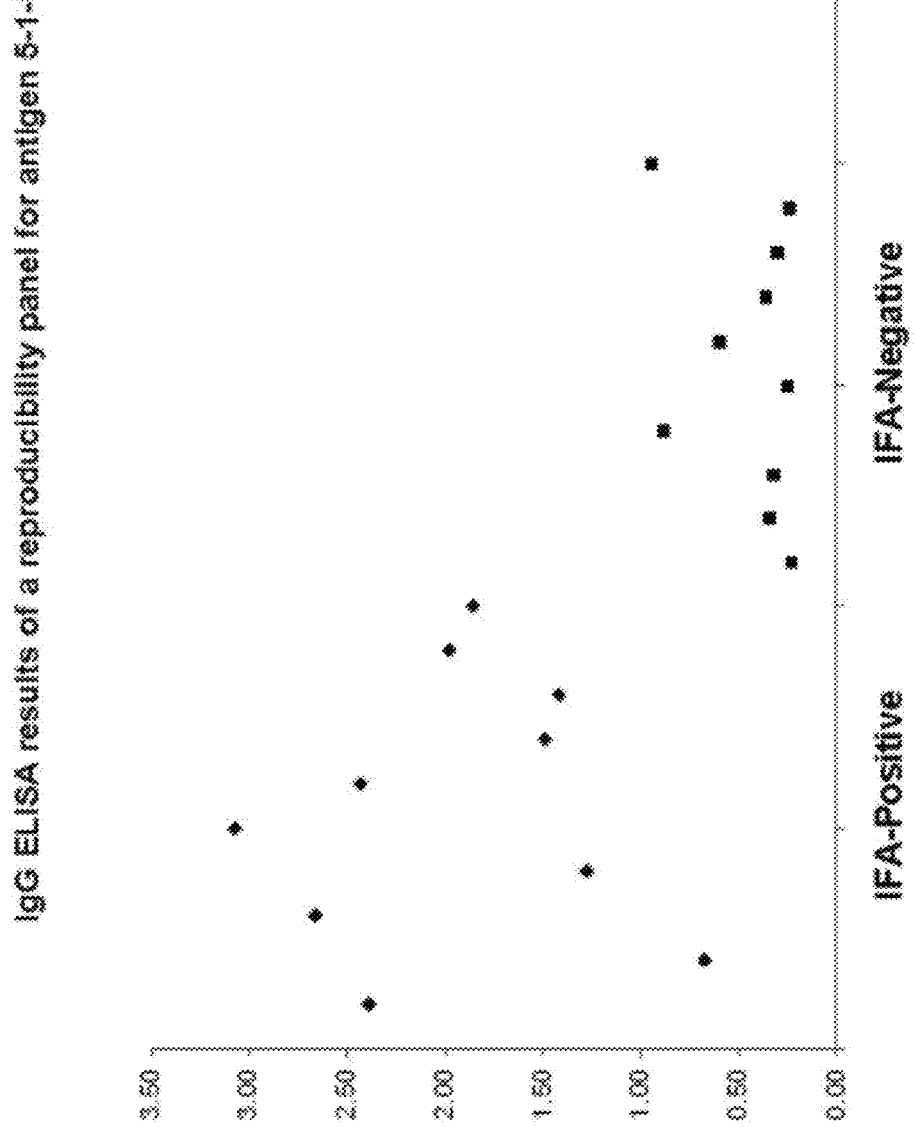
FIG. 13 depicts the IgG ELISA results of a reproducibility panel for antigen 5-1-1. The samples were run by 3 independent operators and results are the average of the three index values. IFA-positive (n=10) samples are represented as ♦ while IFA-negative (n=10) samples are represented as ■. Index values<0.9 are reported as negative, those between 0.9 and 1.1 are reported as equivocal and results>1.1 are reported as positive.

The parameters for the 5-1-1 IgG assay were optimized and the number of patient samples tested was increased to 96. FIG. 12 shows the results of a reproducibility assay in which three individuals performed the assay on the same group of 20 patient samples (Sensitivity and Specificity of 90% and 100%, respectively). One sample gave an equivocal result and one sample tested negative although a positive result was expected based on the IFA data. A patient testing as equivocal should be retested in order to determine if their titer is rising.

In order to identify acute or very recent active infections, an IgM assay is also required. The method described in this application for the IgG assay, whereby the babesial antigen was fixed to the plate was not experimentally effective as IgM antibodies are less specific and a high background level was observed. Therefore, an IgM capture ELISA assay was developed. In this assay, anti-human IgM antibody was coated onto 96 well plates. IFA positive and negative patient sera were then added to the plates. Biotinylated protein 5-1-1 was then reacted to the serum antibody bound to the plate and detected with streptavidin linked to alkaline phosphatase (FIG. 14). This assay successfully distinguished IFA-positive from IFA-negative patient sera. Although there were several samples that gave equivocal results (three negatives and three positives) there were no false negative or false positive outcomes based on the IFA data. Lyme (*Borrelia burgdorferi*) positive patients that were also IFA-negative for *B. microti* were tested and did not cross react in this assay.

In sum, the sensitivity and specificity of the IgG ELISA is 90% and 100%, respectively. The sensitivity and specificity of the IgM ELISA is 100% and 100%, respectively.

EXPERIMENTAL PROTOCOLS

I. Construction of *B. microti* Genomic Library

A lambda phage library of *Babesia microti* DNA was constructed with the lambda ZAP II EcoRI/CIAP-treated vector kit (Stratagene, La Jolla, Calif.). Genomic DNA was isolated from infected hamster blood using the QIAamp DNA blood kit (QIAGEN, Valencia, Calif.). Genomic DNA was digested with EcoRI, precipitated with isopropanol/sodium acetate, washed with 70% ethanol, and the pellet resuspended in TE (pH 8.0). 150 ng of digested DNA was ligated into the pBluescript SK(–) vector (predigested with EcoRI) according to the manufacturer's recommended protocol (Stratagene, La Jolla, Calif.). The recombinant phage concatemers were then packaged into phage using the Gigapack III packaging extract (Stratagene, La Jolla, Calif.). The resulting library was titered by plating with XL-1 Blue *E. coli* (Statagene, La Jolla, Calif.) on NZY agar plates according to the manufacturer's instructions to determine ideal screening density.

II. Genomic Library Screening

The *Babesia* library was plated onto NZY agar plates in *E. coli* strain XL-1 Blue MRF- and plaques were allowed to develop for 8 hours. Nitrocellulose membranes were soaked for 15 minutes in 100 mM IPTG and plaques were transferred to the membranes by incubation at 37° C. for 3 hours. The membranes were washed in PBS-tween (0.05% Tween 20) and blocked overnight in 1% BSA in PBS. Positive plaques were identified by immunoblotting with pooled positive sera obtained from the IFA-positive control sold by Fuller Laboratories (Fullerton, Calif.) at a final dilution of 1:500. Positives were detected using anti-human IgG HRP (KPL, Gaithersburg, Md.) secondary antibody at a dilution of 1:2,000 and developed with DAB substrate (0.5 mgs DAB/ml TBS plus 0.03% hydrogen peroxide). The DAB substrate solution was used to visualize positive spots on the membranes which corresponded to plaques expressing immuno-reactive proteins. Positive plaques were excised from the agar and placed into SM buffer with 4% chloroform. They were then replated at a lower density in a mixture of XLOLR and XPORT *E. coli* strains as well as 704 helper phage and rescreened with the positive sera in order to obtain single plasmids. Positive plaques were identified and grown in overnight cultures for plasmid DNA isolation. Plasmid DNA was digested with EcoRI to ensure single inserts and submitted for cycle sequencing using an Applied Biosystems 3130XL (Foster City, Calif.). Sequence information was used to identify likely antigenic candidates based upon homology.

III. Protein Production

Primers were designed to clone the antigens identified through the library screen (O-1-1 76 and 5-1-1) into the pET 30 Ek-LIC expression vector (Novagen, San Diego, Calif.). Protein expression in transformed BL21 cells was induced using the Overnight Express™ AutoInduction System (Novagen, San Diego, Calif.). Proteins were purified by passage over a Ni-NTA resin column (Novagen, San Diego, Calif.). The protein was concentrated using an Amicon (Millipore, Billerica, Mass.) with a MWCO of 5,000 and stored for use at –20° C.

IV. Western Blotting

Purified protein was electrophoresed through a 15% SDS-PAGE gel at 160 volts for 50 minutes. The protein was transferred onto PVDF membrane for 60 minutes at 100 volts using a mini trans-blot cell (Biorad, Hercules, Calif.). Membranes were blocked in 1% BSA for 1 hour at room temperature. Primary antibodies were IFA-positive and IFA-negative sera that were diluted 1:250 and incubated for 90 minutes at room temperature with the blot. Antigen-specific antibodies were detected by goat anti-human IgG-AP at a dilution of 1:3,000 (Southern Biotech, Birmingham, Ala.) and developed with ready to use NBT/BCIP substrate (Moss, Pasadena, Md.).

V. Human Serum

Patient sera samples used for ELISA development were Babesia IFA-positive and negative human serum purchased from NY Biologics. All samples were confirmed to be positive or negative in-house using Babesia IFA slides and control IgG or IgM sera purchased from Fuller Laboratories.

VI. IgG ELISA

Purified protein was diluted in coating buffer (0.015 M $Na_2CO_3$, 0.035 M $NaHCO_3$ [pH 9.6]) and adhered to 96-well Immulon 2 high-binding plates (DYNEX Technologies, Chantilly, Va.) at 1 µg/ml. After overnight incubation at 4° C., the plates were washed with PBS-Tween 20, blocked with 1% BSA for 1 hour at room temperature, and washed again. Dilutions of serum in 1% bovine serum albumin were added and then incubated for 90 minutes at room temperature. Antigen-specific antibodies were detected by goat anti-human IgG-AP (Southern Biotech, Birmingham, Ala.) and developed with pNPP (Moss, Pasadena, Md.) for 15 min. The reaction was stopped with 1N NaOH and the absorbance at 405 nm was recorded.

VII. Biotinylation of 5-1-1

In order to incorporate 4-6 biotin groups per antigenic protein as suggested by the manufacturer, 1-10 mg/ml of recombinant protein in a 20-fold molar excess of biotin was used. Immediately before use, 10 mM Sulfo-NHS-biotin solution was prepared and added to the protein solution. The reaction was incubated on ice for two hours. The Zeba desalting column was placed in a 15 ml conical tube and equilibrated with PBS. The protein solution was added to the equilibrated column and centrifuged to desalt the protein solution. The HABA assay was used to determine the efficiency of the biotin incorporation according to the manufacturer's (Pierce, ThermoFisher) instructions. Briefly, HABA/Avidin solution was made and added into microplate wells in duplicate. In separate wells biotinylated protein was added HABA/Avidin solution. The plate was incubated for 10 minutes on a shaker and the absorbance read at 500 nm. Mole of biotin per mole of protein was calculated using the HABA calculator found on the Pierce website.

VIII. IgM Capture ELISA

Anti-human IgM (KPL, Gaitherberg, Md.) was diluted in coating buffer and adhered to 96-well Maxisorb plates (VWR, West Chester, Pa.). After overnight incubation at 4° C., the plates were washed with PBS-Tween 20, blocked with 1% BSA for one hour at room temperature and washed again. Serum samples were diluted 1:100 and added to the plates for one hour at room temperature. Biotinylated 5-1-1 was then reacted to the plates for one hour at room temperature with shaking The plates were detected with streptavidin-alkaline phosphatase (Southern Biotech, Birmingham, Ala.) and developed with ready to use pNPP substrate (Moss, Pasadena, Md.) for 15 minutes. The reaction was stopped with 1N NaOH and the absorbance at 405 nm was recorded.

Although the invention has been described in example embodiments, additional modifications and variations would be apparent to those skilled in the art. It is therefore to be understood that the inventions herein may be practiced other than as specifically described. Thus, the present embodiments should be considered in all respects as illustrative and not restrictive. Accordingly, it is intended that such changes and modifications fall within the scope of the present invention as defined by the claims appended hereto.

REFERENCES

1) Adelson, M. E., Rao, R. V., Tilton, R. C., Cabets, K., Eskow, E., Fein, L., Occi, J. L. and Mordechai, E. (2004) Prevalence of Borrelia burgdorferi, Bartonella spp., Babesia microti, and Anaplasma phagocytophila in Ixodes scapularis ticks collected in Northern New Jersey. J Clin Microbiol 42, 2799-801.

2) Anderson, J. F., Mintz, E. D., Gadbaw, J. J. and Magnarelli, L. A. (1991) Babesia microti, human babesiosis, and Borrelia burgdorferi in Connecticut. J Clin Microbiol 29, 2779-83.

3) Horner, M. J., Aguilar-Delfin, I., Telford, S. R., 3rd, Krause, P. J. and Persing, D. H. (2000) Babesiosis. Clin Microbiol Rev 13, 451-69.

4) Homer, M. J., Lodes, M. J., Reynolds, L. D., Zhang, Y., Douglass, J. F., McNeill, P. D., Houghton, R. L. and Persing, D. H. (2003) Identification and characterization of putative secreted antigens from Babesia microti. J Clin Microbiol 41, 723-9.

5) Krause, P. J., Ryan, R., Telford, S., 3rd, Persing, D. and Spielman, A. (1996a) Efficacy of immunoglobulin M serodiagnostic test for rapid diagnosis of acute babesiosis. J Clin Microbiol 34, 2014-6.

6) Krause, P. J., Telford, S. R., 3rd, Ryan, R., Conrad, P. A., Wilson, M., Thomford, J. W. and Spielman, A. (1994) Diagnosis of babesiosis: evaluation of a serologic test for the detection of Babesia microti antibody. J Infect Dis 169, 923-6.

7) Krause, P. J., Telford, S. R., 3rd, Spielman, A., Sikand, V., Ryan, R., Christianson, D., Burke, G., Brassard, P., Pollack, R., Peck, J. and Persing, D. H. (1996b) Concurrent Lyme disease and babesiosis. Evidence for increased severity and duration of illness. Jama 275, 1657-60.

8) Leiby, D. A., Chung, A. P., Gill, J. E., Houghton, R. L., Persing, D. H., Badon, S, and Cable, R. G. (2005) Demonstrable parasitemia among Connecticut blood donors with antibodies to Babesia microti. Transfusion 45, 1804-10.

9) Lodes, M. J., Houghton, R. L., Bruinsma, E. S., Mohamath, R., Reynolds, L. D., Benson, D. R., Krause, P. J., Reed, S. G. and Persing, D. H. (2000) Serological expression cloning of novel immunoreactive antigens of Babesia microti. Infect Immun 68, 2783-90.

10) Magnarelli, L. A., Anderson, J. F., Stafford, K. C., 3rd and Dumler, J. S. (1997) Antibodies to multiple tick-borne pathogens of babesiosis, ehrlichiosis, and Lyme borreliosis in white-footed mice. J Wildl Dis 33, 466-73.

11) Magnarelli, L. A., Stafford, K. C., 3rd, Ijdo, J. W. and Fikrig, E. (2006) Antibodies to whole-cell or recombinant antigens of Borrelia burgdorferi, Anaplasma phagocytophilum, and Babesia microti in white-footed mice. J Wildl Dis 42, 732-8.

12) Persing, D. H., Mathiesen, D., Marshall, W. F., Telford, S. R., Spielman, A., Thomford, J. W. and Conrad, P. A. (1992) Detection of Babesia microti by polymerase chain reaction. J Clin Microbiol 30, 2097-103.

13) Quick, R. E., Herwaldt, B. L., Thomford, J. W., Garnett, M. E., Eberhard, M. L., Wilson, M., Spach, D. H., Dickerson, J. W., Telford, S. R., 3rd, Steingart, K. R., Pollock, R., Persing, D. H., Kobayashi, J. M., Juranek, D. D. and Conrad, P. A. (1993) Babesiosis in Washington State: a new species of Babesia? Ann Intern Med 119, 284-90.

14) Ryan, R., Krause, P. J., Radolf, J., Freeman, K., Spielman, A., Lenz, R. and Levin, A. (2001) Diagnosis of babesiosis using an immunoblot serologic test. Clin Diagn Lab Immunol 8, 1177-80.

15) Telford, S. R., 3rd and Goethert, H. K. (2004) Emerging tick-borne infections: rediscovered and better characterized, or truly 'new'? Parasitology 129 Suppl, S301-27.

What is claimed is:

1. An isolated polypeptide having an amino acid sequence selected from the group consisting of SEQ ID NO: 2 and SEQ ID NO: 4.

2. The isolated polypeptide of claim 1, wherein said amino acid sequence is SEQ ID NO: 2.

3. The isolated polypeptide of claim 1, wherein said amino acid sequence is SEQ ID NO: 4.

4. A composition comprising the isolated polypeptide of claim 1 and a support.

5. The composition of claim 4, wherein said support is selected from the group consisting of polyethylene, polypropylene and glass.

6. The composition of claim 4, wherein said support is a microtiter well.

7. A kit comprising the isolated polypeptide of claim 1 and a packaging material.

8. The kit of claim 7, wherein said packaging material comprises an instruction for detecting the presence of an antibody against *Babesia microti*.

* * * * *